(12) United States Patent
Moriyama et al.

(10) Patent No.: US 7,785,633 B2
(45) Date of Patent: Aug. 31, 2010

(54) AGENT FOR PREVENTING OR SUPPRESSING HEPATOPATHY AND FUNCTIONAL FOOD FOR PREVENTING OR SUPPRESSING HEPATOPATHY

(75) Inventors: Yoshinori Moriyama, Okayama (JP); Seiji Tsuboi, Okayama (JP); Akihiro Masuyama, Sagamihara (JP); Toshiaki Takano, Kawasaki (JP); Teppei Nakamura, Sagamihara (JP)

(73) Assignee: Calpis Co., Ltd, Tokyo (JP)

( * ) Notice: Subject to any disclaimer, the term of this patent is extended or adjusted under 35 U.S.C. 154(b) by 0 days.

(21) Appl. No.: 11/952,822

(22) Filed: Dec. 7, 2007

(65) Prior Publication Data

US 2008/0085321 A1 Apr. 10, 2008

Related U.S. Application Data

(63) Continuation of application No. 10/599,447, filed as application No. PCT/JP2005/006243 on Mar. 31, 2005, now abandoned.

(30) Foreign Application Priority Data

Mar. 31, 2004 (JP) ............................. 2004-106105

(51) Int. Cl.
*A61K 35/20* (2006.01)
(52) U.S. Cl. .................................. 424/535; 424/93.45
(58) Field of Classification Search .................. None
See application file for complete search history.

(56) References Cited

U.S. PATENT DOCUMENTS

| | | | |
|---|---|---|---|
| 5,710,132 A | 1/1998 | Moller et al. | |
| 6,262,019 B1 | 7/2001 | Keller et al. | |
| 6,225,104 B1 | 11/2001 | Cavaliere Vesely et al. | |
| 6,534,304 B1 * | 3/2003 | Yamamoto et al. | 435/252.9 |
| 6,827,953 B1 * | 12/2004 | Mizutani et al. | 426/62 |

FOREIGN PATENT DOCUMENTS

| | | |
|---|---|---|
| EP | 0 825 869 B1 | 3/1998 |
| JP | 01-268641 | 10/1989 |
| JP | 05-176713 | 7/1993 |
| JP | 05-344864 | 12/1993 |
| JP | 08-0999 | 4/1996 |
| JP | 09-301887 | 11/1997 |
| JP | 1198978 A | 4/1999 |
| JP | 2000-189105 | 7/2000 |
| JP | 2000-197469 | 7/2000 |
| JP | 2002-226289 | 8/2001 |
| JP | 2002-332242 | 11/2002 |
| WO | WO 01-328836 A1 | 5/2001 |
| WO | WO 02-43753 A1 | 6/2001 |
| WO | WO 03-090546 A1 | 11/2003 |
| WO | 2004/047566 A1 | 6/2004 |

OTHER PUBLICATIONS

Satake et al., Biosci. Biotechnol. Biochem. 2002, vol. 66(2), p. 378-384.*
Lee, W. M., The New England Journal of Medicine, 2003, vol. 349, p. 474-485.*
Kajimoto et al., Journal of Nutritional Food, 2001, vol. 4 No. 3, p. No. 1-6 and 8-15.*
Heuman et al., Gastroenterology, 1991, vol. 100, No. 1, Abstract.*
Zommara et al., Nutrition Research, 1996, vol. 16, No. 2, p. 293-302.*
Database Calpus on STN, Abstract No. 2001-79928 Abstract & Barreto. R., et al., "Experimental Acute Alcohol Pancreatitis-Related Liver Damage and Exdotoxinemia; Protective Effect of Aprobiaotic But Not of Metronidazole", International Medical Journal (2000)vol. 7. No. 4, pp. 251 to 256.
Bulletin of Japan Dairy Technical Association; vol. 51-2001; pp. 1-21; Lactoferrin in Milk; Kei-Ichi Shimazaki; Dairy Science Laboratory; Department of Animal Product Science; Graduate School of Agriculture; Hokkaido University; Kita-9, Nishi-9, Kita-Ku, Sapporo 060-8589.
Heat Stability of Bovine Lactoferrin at Acidic pH; Hiroaki Abe, et al; Nutritional Science Library; 1991 J. Dairy Sci 74:65-71.

* cited by examiner

*Primary Examiner*—L Blaine Lankford
*Assistant Examiner*—Kade Ariani
(74) *Attorney, Agent, or Firm*—Sughrue Mion, PLLC

(57) ABSTRACT

The present invention provides an agent for preventing or suppressing hepatic dysfunction which may be taken daily and continuously, has excellent safety, and is capable of effectively preventing and/or suppressing hepatic dysfunction, such as hepatocellular necrosis, and functional food, such as foods for specified health uses, for preventing or suppressing hepatic dysfunction containing this agent. The agent for preventing or suppressing hepatic dysfunction of the present invention contains whey as the active component, and the functional food for preventing or suppressing hepatic dysfunction contains the agent for preventing or suppressing hepatic dysfunction.

10 Claims, No Drawings

AGENT FOR PREVENTING OR SUPPRESSING HEPATOPATHY AND FUNCTIONAL FOOD FOR PREVENTING OR SUPPRESSING HEPATOPATHY

This is a continuation of application Ser. No. 10/599,447 filed Feb. 9, 2007 now abandoned which is a 371 of PCT/JP2005/006243 and which claims the priority of Japanese Application JP 2004-106105 filed Mar. 31, 2004, all of which are considered part of the disclosure of the accompanying application and are hereby incorporated by reference.

FIELD OF ART

The present invention relates to an agent for preventing or suppressing hepatic dysfunction, and functional food, such as foods for specified health uses, for preventing or suppressing hepatic dysfunction. In particular, the present invention relates to an agent and functional food for preventing or suppressing hepatic dysfunction, which suppress the elevation of serum GOT and GPT levels caused by hepatocellular necrosis to prevent and/or suppress hepatic dysfunction.

BACKGROUND ART

Liver is a central organ of metabolism, and has a variety of important functions, such as biligenesis, excretion, detoxication, and the like. On the other hand, liver is said to be a silent organ due to its great reserve, and hardly develops symptoms, such as malaise, jaundice, edema, and ascites, so that its dysfunction tends to be perceived too late. It is generally known that an abundance of GOT (glutamic-oxaloacetic transaminase) and GPT (glutamic-pyruvic transaminase) are present in liver, and the blood GOT and GPT levels sensitively reflect the degree of hepatocellular necrosis, so that these levels are often used as convenient means for evaluating hepatic dysfunction.

Recent westernization of dietary habit, nutritional unbalance, and ingestion of alcohol or drugs have imposed increasing burden on liver, resulting in substantial increase in the number of patients suffering from fatty liver. Chronic liver diseases progress through repeated hepatocellular destruction and regeneration over years to cause hepatic fibrosis, and lead to cirrhosis or hepatocellular carcinoma. Patients suffering from such disease are also increasing.

There is no effective drug for liver diseases at present, and diet therapy and rest are the prevailing therapy. Though, for example, glycyrrhizin formulation, such as Stronger Neo-Minophagen C (registered trade mark, manufactured by MINOPHAGEN PHARMACEUTICAL, CO., LTD.) is sometimes used for chronic liver diseases, such glycyrrhizin formulation is inactivated in the intestines, so that desired effect cannot be expected through oral administration, and parenteral injection is the main route of administration. Thus patients suffer from regular injections, and even side effects, such as hypertension or hypokalemia, are reported to be produced.

On the other hand, various amino acid formulations are sometimes used for the purpose of ameliorating hepatic encephalopathy or hypoalbuminemia associated with liver diseases such as cirrhosis or hepatic insufficiency. However, such amino acid formulations are used with mere expectation of improvement in nutritional deficiency caused by liver diseases, i.e., improvement in nitrogen metabolism or reduction of blood ammonia level by balancing the plasma amino acid, rather than treatment of liver diseases.

There has recently been proposed an agent for improving liver function containing lactoperoxidase and/or lactoferrin as an active component (see Patent Publication 1). Lactoferrin is known to be contained in milks of various mammals.

However, lactoferrin is prone to thermal denaturation, and known to be denatured easily in ordinary high temperature pasteurization or the like process (see, for example, Non-patent Publications 1 to 3). Thus isolation or use of lactoferrin in industrial scale is restricted, and problems remain in cost and versatility.

Whey has recently come to be known to contain various components having physiological functions, such as components for protecting gastric mucosa ($\alpha$-lactalbumin) However, no improving effect on liver function has been reported of milk or whey that has undergone ordinary pasteurization.

Patent Publication 1: JP-2001-226289-A

Non-patent Publication 1: Shokuhin Shinsozai Yuukou Riyou Gijutsu Series "Lactoferrin" (March 2000, Shadan Houjin Kashi Sougou Gijutsu Center)

Non-patent Publication 2: Nyugyo Gijutsu, Vol. 51, 2001, "Miruku no Rakutoferin (Lactoferrin in Milk)"

Non-patent Publication 3: Journal of Dairy Science Vol. 74, No. 1, p 65-71, 1991

SUMMARY OF THE INVENTION

It is an object of the present invention to provide an agent for preventing or suppressing hepatic dysfunction which may be taken daily and continuously, has excellent safety, and is capable of effectively preventing and/or suppressing hepatic dysfunction, such as hepatocellular necrosis, and functional food, such as foods for specified health uses, for preventing or suppressing hepatic dysfunction containing this agent.

According to the present invention, there is provided an agent for preventing or suppressing hepatic dysfunction comprising whey as an active component.

According to the present invention, there is also provided functional food for preventing or suppressing hepatic dysfunction comprising the above agent for preventing or suppressing hepatic dysfunction.

According to the present invention, there is provided a method for preventing or suppressing hepatic dysfunction comprising the step of orally administering to an animal in need thereof an effective amount of an agent for preventing or suppressing hepatic dysfunction comprising whey as an active component.

According to the present invention, there is also provided use of whey for the manufacture of an agent for preventing or suppressing hepatic dysfunction.

According to the present invention, there is further provided use of whey for the manufacture of functional food for preventing or suppressing hepatic dysfunction.

Since the agent for preventing or suppressing hepatic dysfunction according to the present invention contains whey, which has been taken as food, as the active component, the agent may be taken daily and continuously, is excellently safe, and may effectively prevent and/or suppress hepatic dysfunction, such as hepatocellular necrosis. Since the functional food for preventing or suppressing hepatic dysfunction according to the present invention contains the present agent for preventing or suppressing hepatic dysfunction, the present functional food may be expected to prevent and/or suppress hepatic dysfunction.

PREFERRED EMBODIMENTS OF THE INVENTION

The present invention will now be explained in detail.

The agent for preventing or suppressing hepatic dysfunction according to the present invention contains whey as the active component, and is capable of effectively preventing and/or suppressing, for example, the elevation of blood GOT and GPT levels, which is said to be ascribable mainly to hepatocellular necrosis.

The active component, whey, includes an aqueous fraction of milk obtained by removing all or most of the casein protein and the like from milk according to a common procedure, and may be, for example, acid whey and/or cheese whey. Examples of the acid whey may include fermented milk whey obtained by fermentation of milk with lactic acid bacteria, and casein whey containing an aqueous fraction of milk obtained by adding acid to milk to remove all or most of the casein protein and the like according to a common procedure. Fermented milk whey is particularly preferred for its excellent ability to prevent and/or suppress hepatic dysfunction.

The fermented milk whey may usually be a fermented milk whey prepared by fermentation of milk with lactic acid bacteria, or by symbiotic fermentation of milk with lactic acid bacteria and a yeast. The starting material milk may be animal milk, such as cow's milk, goat's milk, or sheep's milk; vegetable milk, such as soy bean milk; or processed milk thereof, such as skim milk, reconstituted milk, powdered milk, or condensed milk. The milk may be in the form of a mixture.

The solid content of the milk is not particularly limited. For example, for skim milk, the solid non-fat content is typically about 9 mass %. On the other hand, considering the per-plant productivity, the solid non-fat content may be increased to some extent. The fermented milk whey obtained in the production of fermented milk may be separated from other milk components before use, but when the fermented milk whey is to be made into the functional food or the like to be discussed later, such other milk components are not necessarily separated.

The lactic acid bacteria may be those of the genus *Streptococcus, Lactococcus, Lactobacillus, Bifidobacterium*, or the like, with *Lactobacillus* being preferred. Specific examples of *Lactobacillus* may include *Lactobacillus bulgaricus, Lactobacillus helveticus, Lactobacillus casei, Lactobacillus acidophilus*, and *Lactobacillus fermentum*, with *Lactobacillus helveticus* being particularly preferred. More specifically, *Lactobacillus helveticus* ATCC 15009, *Lactobacillus helveticus* ATCC 521, and *Lactobacillus helveticus* CM4 strain (deposited at National Institute of Advanced Industrial Science and Technology, International Patent Organism Depositary under Accession Number FERM BP-6060 on Aug. 15, 1997) (referred to as CM4 hereinbelow) may be used, with CM4 being particularly preferred. CM4 has been deposited under the above-mentioned accession number under the Budapest Treaty on the International Recognition of the Deposit of Microorganisms for the Purposes of patent Procedure. All restrictions on the availability to the public of this strain will be irrevocably removed upon the granting of a patent.

The lactic acid bacteria are preferably in the form of a pre-cultured starter having sufficiently high activity. The initial cell count may preferably be about $10^5$-$10^7$ cells/ml.

When the fermented milk whey is to be used in functional food, such as foods for specified health uses, yeast may be used for symbiotic fermentation for improved flavor and palatability. The strain of the yeast is not particularly limited, and may preferably be, for example, yeast of the genus *Saccharomyces*, such as Saccharomyces cerevisiae. The content of the yeast may suitably be selected depending on the purpose.

The fermentation may be carried out by culturing one or more kinds of the lactic acid bacteria in a medium, or culturing a mixture of one or more kinds of the lactic acid bacteria and one or more kinds of the yeast in a medium. The medium may be those composed only of one or more kinds of the milk components mentioned above, or those optionally contain additional components, such as yeast extract; vitamins, e.g. ascorbic acid; amino acids, e.g. cysteine; salts, e.g. sodium-chloride; sugars, e.g. glucose, sucrose, raffinose, or stachyose; stabilizers, e.g. gelatine; and flavoring agents.

The fermentation may be performed usually by static or stirred culture, for example at 20 to 50° C., preferably 30 to 45° C., at the initial pH of 6.0 to 7.0, and may be terminated when the cell count becomes $10^7$ cells/ml or higher at pH 5.0 or lower. The milk may be subjected to high-temperature pasteurization before fermentation.

The fermented milk whey may be separated from curd by means of a common separating operation. On the other hand, when the fermented milk whey as the active component is to be used in the functional food to be discussed later, the fermented milk containing the whey may be used as it is without separation, if so desired, or the extent of separation may suitably be decided.

The casein whey may be prepared by, when solid milk, such as whole milk or skim milk is used, dissolving the milk in distilled water, adding, for example, lactic acid, citric acid, acetic acid, tartaric acid, fumaric acid, malic acid, gluconic acid, or adipic acid to adjust the acidity to a level suitable for removing protein, typically casein, and separating the whey component (aqueous fraction) by a common procedure, such as membrane filtration. Here, the milk may be subjected to high temperature pasteurization before the acid is added. The acid may usually be added in an amount for achieving 1.0 to 4.0% acidity, depending on the kind of the acid or the like.

The cheese whey may be prepared in the ordinary cheese production, by coagulating milk with rennet to form curd, and separating the whey component from the curd by centrifugation or the like. Here, the milk may be subjected to high temperature pasteurization before the rennet is added.

The dose of the whey as the active component in the present agent for preventing or suppressing hepatic dysfunction is not particularly limited, taking the continuity of administration into account, and may usually be not less than 0.01 g per kg body weight per day, preferably not less than 0.01 g per kg body weight per day, in terms of freeze-dried powder. Further, the agent for preventing or suppressing hepatic dysfunction of the present invention may optionally contain components other than the whey as desired, having the function of preventing or suppressing hepatic dysfunction.

The agent for preventing or suppressing hepatic dysfunction according to the present invention may be in the form of whey with or without processing, for example, a whey concentrate obtained by concentrating whey through vacuum concentration or the like process, or a dried whey powder obtained by drying whey through freeze-drying or spray drying.

The agent for preventing or suppressing hepatic dysfunction according to the present invention may be administered usually through an oral route. For example, the agent may be administered before or after the symptoms of hepatic dysfunction are developed, either continuously or intermittently.

The functional food for preventing or suppressing hepatic dysfunction according to the present invention contains the agent for preventing or suppressing hepatic dysfunction of the present invention.

The functional food may be functional food, such as foods for specified health uses, claiming prevention or suppression of hepatic dysfunction, such as hepatocellular necrosis.

The functional food may optionally contain additives, such as sugars, proteins, lipids, vitamins, minerals, flavoring agents, or mixtures thereof. Further, the milk components from which the whey is separated, may also be contained.

In the functional food of the present invention, the content of the whey as the active component may suitably be selected depending on the form or kind of the food. The content may suitably be selected also depending on the continuity of intake of the functional food or the like factors, and is not particularly limited. A suitable content may be usually 1 to 100 mass %.

The functional food may be in the form of, for example, fermented milk products, such as yoghurt or lactic acid bacteria beverage, processed food and beverage containing whey, dry powders, tablets, capsules, granules, or the like.

The dose and the timing of administration of the functional food of the present invention are not particularly limited, and it is preferred to take the functional food in such an amount that the above-mentioned dose of the active component is generally achieved. For example, the present functional food may be taken continuously or intermittently before or after the symptoms of hepatic dysfunction are developed.

EXAMPLES

The present invention will now be explained in more detail with reference to Examples, which do not intend to limit the present invention.

Examples 1 and 2

Commercially available skim milk was dissolved in distilled water at a solid content of 9 mass %, subjected to high temperature pasteurization in an autoclave at 105° C. for 10 minutes, allowed to cool to the room temperature, inoculated with 3 mass % of a *Lactobacillus helveticus* CM4 starter, and cultured at 37° C. for 24 hours, to thereby obtain fermented milk. This fermented milk was centrifuged at 12000 G for 20 minutes for removing the solids, to prepare fermented milk whey.

On the other hand, commercially available skim milk was dissolved in distilled water at a solid content of 9 mass %, subjected to high temperature pasteurization in an autoclave at 105° C. for 10 minutes, and allowed to cool to the room temperature. Lactic acid was added to increase the acidity to 2.2%. Then the product was centrifuged at 12000 G for 20 minutes for removing the solids, to prepare casein whey.

Each of the obtained fermented milk whey (Example 1) and casein whey (Example 2) was diluted with distilled water to 10 mass %, and used in the following animal test as a drinking water. As a control, distilled water without whey was also used in the test.

Male ICR mice at 3 weeks of age were divided into three groups of 10 animals each, and allowed free access to solid feed (trade name MF, manufactured by ORIENTAL YEAST CO., LTD.), and distilled water, 10 mass % fermented milk whey prepared above, or 10 mass % casein whey prepared above, for 1 month. The mice were then fastened for 18 hours, and each group was subdivided into two subgroups of 5 animals each. The mice were intraperitoneally administered with saline or acetaminophene solution (700 mg/kg). Acetaminophene is used as an antipyretic/analgesic even in popular medicines. However, it is known that acetaminophene, if administered in an excess amount, cannot be processed in liver, resulting in fulminant hepatitis-like hepatic dysfunction. Thus this drug is often used in experiments for evaluation of hepatic dysfunction.

The serum GOT and GPT levels were measured 2 and 4 hours after the administration using Transamirase CII Test Kit (WAKO PURE CHEMICAL INDUSTRIES, LTD.) for evaluating the effect of preventing or suppressing hepatic dysfunction. The results are shown in Table 1.

It is understood from the results in Table 1 that in the control group given distilled water, the serum GOT and GPT levels were remarkably elevated by administration of acetaminophene, whereas in the groups given the fermented milk whey or the casein whey, such elevation was suppressed, so that excellent effect of preventing or suppressing hepatic dysfunction was exhibited. It was particularly noted that, in the group given the fermented milk whey, elevation of the GOT and GPT levels by administration of acetaminophene was suppressed more remarkably than in the group given the casein whey.

TABLE 1

| | | | Level after 2 hours | Level after 4 hours |
|---|---|---|---|---|
| GOT level | Control | Group given water + saline | 164 | 198 |
| | | Group given water + acetaminophene | 577 | 841 |
| | Example 1 | Group given fermented milk whey + saline | 83.9 | 59 |
| | | Group given fermented milk whey + acetaminophene | 125 | 229 |
| | Example 2 | Group given casein whey + saline | 123 | 212 |
| | | Group given casein whey + acetaminophene | 340 | 798 |
| GPT level | Control | Group given water + saline | 11.8 | 28.4 |
| | | Group given water + acetaminophene | 128 | 618 |
| | Example 1 | Group given fermented milk whey + saline | 6.29 | 15.8 |
| | | Group given fermented milk whey + acetaminophene | 6.02 | 30.1 |
| | Example 2 | Group given casein whey + saline | 14.6 | 20.5 |
| | | Group given casein whey + acetaminophene | 40.5 | 110 |

What is claimed is:

1. A method for treating hepatocellular necrosis by administering to a subject in need thereof an effective amount of acid whey obtained by fermentation of animal milk with lactic acid bacteria of the species *Lactobacillus helveticus*.

2. The method for treating hepatocellular necrosis according to claim 1, wherein said *Lactobacillus helveticus* is of a strain *Lactobacillus helveticus* CM4 (deposited at National Institute of Advanced Industrial Science and Technology, International Patent Organism Depositary under Accession Number FERM BP-6060).

3. The method for treating hepatocellular necrosis according to claim 1, wherein an effective amount of said acid whey is administered to the subject after the symptoms of hepatocellular necrosis are developed.

4. The method for treating hepatocellular necrosis according to claim 2, wherein an effective amount of said acid whey is administered to the subject after the symptoms of hepatocellular necrosis are developed.

5. A method for ameliorating hepatocellular necrosis by administering to a subject in need thereof an effective amount of acid whey obtained by fermentation of animal milk with bacteria including lactic acid bacteria of the species *Lactobacillus helveticus*.

6. The method for ameliorating hepatocellular necrosis according to claim 5, wherein said *Lactobacillus helveticus* is of a strain *Lactobacillus helveticus* CM4 (deposited at National Institute of Advanced Industrial Science and Technology, International Patent Organism Depositary under Accession Number FERM BP-6060).

7. The method for ameliorating hepatocellular necrosis according to claim 5, wherein an effective amount of said acid whey is administered to the subject before the symptoms of hepatocellular necrosis are developed.

8. The method for ameliorating hepatocellular necrosis according to claim 5, wherein an effective amount of said acid whey is administered to the subject after the symptoms of hepatocellular necrosis are developed.

9. The method for ameliorating hepatocellular necrosis according to claim 6, wherein an effective amount of said acid whey is administered to the subject before the symptoms of hepatocellular necrosis are developed.

10. The method for ameliorating hepatocellular necrosis, according to claim 6, wherein an effective amount of said acid whey is administered to the subject after the symptoms of hepatocellular necrosis are developed.

* * * * *